United States Patent [19]

Grollier et al.

[11] 4,213,960

[45] Jul. 22, 1980

[54] COSMETIC COMPOSITIONS FOR TREATING THE HAIR

[75] Inventors: Jean-Francois Grollier; Claire Fiquet; Chantal Fourcadier, all of Paris; Claude Dubief, Versailles; Danièle Cauwet, Crosne, all of France

[73] Assignee: L'Oreal, Paris, France

[21] Appl. No.: 882,424

[22] Filed: Mar. 1, 1978

[30] Foreign Application Priority Data

Mar. 2, 1977 [FR] France ............................ 77 06032

[51] Int. Cl.$^2$ .............................................. A61K 7/06
[52] U.S. Cl. .......................................... 424/47; 8/405; 8/554; 424/DIG. 1; 424/DIG. 2; 424/70; 424/71
[58] Field of Search ................ 424/DIG. 2, DIG. 1, 424/47, 70, 71; 8/10, 11, 10.1, 10.2, 32

[56] References Cited

U.S. PATENT DOCUMENTS

| | | | |
|---|---|---|---|
| 3,560,609 | 2/1971 | Korden | 424/72 |
| 3,560,610 | 2/1971 | Korden | 424/72 |
| 3,632,559 | 1/1972 | Matter et al. | 260/785 C |
| 3,773,056 | 11/1973 | Kalopissis et al. | 132/7 |
| 3,893,803 | 7/1975 | Kaiser | 8/10.2 |
| 3,912,808 | 10/1975 | Sokol | 424/71 |
| 3,957,424 | 5/1976 | Zeffren et al. | 8/10.2 |
| 3,986,825 | 10/1976 | Sokol | 8/10.1 |
| 4,027,008 | 5/1977 | Sokol | 424/62 |

FOREIGN PATENT DOCUMENTS

| | | | |
|---|---|---|---|
| 2252840 | 6/1971 | France | 424/71 |
| 2080759 | 11/1971 | France | 424/71 |
| 2112550 | 6/1972 | France | 8/10.2 |
| 2132214 | 11/1972 | France | 8/10.2 |

*Primary Examiner*—Howard T. Mars
*Assistant Examiner*—Vera C. Clarke
*Attorney, Agent, or Firm*—Fleit & Jacobson

[57] ABSTRACT

The invention relates to cosmetic compositions for conditioning the hair, which contain polyaminoamides and quaternary ammonium homopolymers or compolymers.

30 Claims, No Drawings

COSMETIC COMPOSITIONS FOR TREATING THE HAIR

The present invention relates to cosmetic compositions which can be used for treating the hair.

Hair is generally degraded to varying extents by the action of atmospheric agents and also by the action of such treatments as bleaching, permanent waving and dyeing. As a result, the hair is frequently difficult to comb out and to style, and even voluminous heads of hair do not easily retain a good-looking style, principally due to the fact that the hair is lacking in strength and springiness.

It has already been proposed to overcome these difficulties by applying to the hair so-called "conditioning" agents, which make the wet hair easier to disentangle and to comb, which ensure that the style holds well and which, after drying, impart body, bulk and elasticity to the hair.

Polymers of the polyamino-amide type, for example those described in U.S. Pat. No. 3,632,559 can be used for this purpose. These polyamino-amides are very valuable "conditioning" agents which render the hair springy and ensure that the style has volume and holds well. However, it has been found that the repeated application of these conditioning agents, while still enabling the style to hold well and while still imparting bulk and elasticity to the hair, gives the hair a rough feel, more particularly on the most sensitized parts.

We have now discovered, according to this invention, that this undesired effect can be prevented by using crosslinked polyamino-amides in combination with particular cationic agents which are quaternary ammonium homopolymers or copolymers, without decreasing the conditioning effect of the polyamino-amides. Accordingly the present invention provides a cosmetic composition suitable for application to the hair which contains at least one hydrosoluble crosslinked polyamino-amide resulting from the condensation of a polyalkylene-polyamine with a polycarboxylic acid, followed by alkylation with a bifunctional agent and at least one cationic agent which is a water-soluble high molecular weight quaternary ammonium homopolymer or copolymer as defined below, as well as a process for treating the hair, which comprises applying such a composition thereto.

The cosmetic compositions of this invention which are intended to be applied to keratin fibres, preferably to human hair, are generally in the form of an aqueous or aqueous-alcoholic solution, a cream, a gel or an emulsion.

Suitable alcohols include lower alkanols, preferably those having 1 to 4 carbon atoms, especially ethanol or isopropanol.

High molecular weight means especially in the present specification a weight comprised between 20,000 and 3,000,000 and preferably between 50,000 and 2,000,000.

The homopolymers used in the composition contain, as the main constituent of the chain, quaternary units corresponding to the formula:

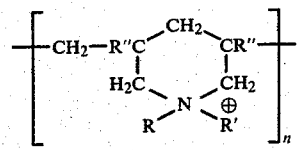

in which R" denotes hydrogen or methyl, and R and R' denote, independently of one another, an alkyl group having from 1 to 22 carbon atoms, a hydroxyalkyl group in which the alkyl group preferably has 1 to 5 carbon atoms, or a lower amidoalkyl group, or R and R' denote, together with the nitrogen atom to which they are bonded, a heterocyclic group such as a piperidinyl or morpholinyl group, in association with a cosmetically acceptable anion, lower alkyl means a 1 to 5 carbon atoms group.

Suitable copolymers for use in the composition of this invention include copolymers of acrylamide or diacetone with monomers providing the units of formula (I).

Suitable polyamino-amides are, more particularly, products resulting from the reaction of polyalkylenepolyamines which contain two primary amino groups, at least one secondary amino group and alkylene groups containing 2 to 4 carbon atoms, with a dicarboxylic acid corresponding to the formula:

$$HOOC-C_mH_{2m}-COOH$$

in which m denotes an integer from 4 to 8, especially adipic acid, or with a derivative of such an acid. The molar ratio of these reactants is preferably from 4:5 to 6:5.

The polyamide resulting from this reaction is alkylated with a bifunctional alkylating agent typically corresponding to the formula:

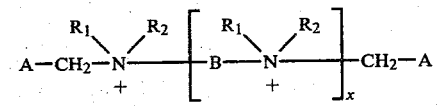

in which x denotes 0 or an integer from 1 to 7, A denotes a group

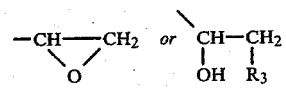

in which $R_3$ denotes halogen, preferably chlorine or bromine, $R_1$ and $R_2$ each independently denotes an alkyl or hydroxyalkyl group containing 1 to 4 carbon atoms, and B represents an alkylene radical containing 2 to 6 carbon atoms, a radical

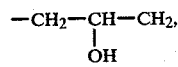

or a radical $-(CH_2)_y-NH-CO-NH-(CH_2)_y-$ in which y is an integer from 1 to 4.

The polymers which are particularly preferred are those in which A denotes

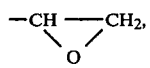

$R_1$ and $R_2$ denote a said lower alkyl group, in particular, methyl, and x is equal to 0.

The amount of bifunctional alkylating agent is such that polyamino-amide derivatives are formed which have a high molecular weight but are soluble in water.

Such polymers are described, inter alia, in U.S. Pat. No. 3,632,559, the disclosure of which is hereby incorporated in its entirety by reference.

Preferred polymers of this type, for the purpose of the present invention, are adipic acid/dialkylaminohydroxyalkyl-dialkylenetriamine copolymers in which the alkyl radical contains 1 to 4 carbon atoms, preferably methyl, ethyl or propyl. Other compounds which make it possible to obtain particularly good results are adipic acid/dimethylaminohydroxypropyl-diethylenetriamine copolymers sold under the tradename "Cartarétine" F, $F_4$ or $F_8$ by Messrs. SANDOZ.

These copolymers generally have a nitrogen content of 17.0 to 18.0% by weight (dry basis), and a viscosity, in a 30% by weight aqueous solution at 20° C. of 350 to 800 centipoises, determined with a Brookfield viscometer using a No. 3 spindle at 30 revolutions per minute.

The cationic agents which are used with the polyamino-amides include the acetate, borate, bromide, chloride, citrate, tartrate, bisulphate, bisulphite, sulphate, phosphate or succinate ion. Such compounds are described, in particular, in U.S. Pat. Nos. 3,912,808, 3,986,825, 4,027,008, the disclosure of which is hereby incorporated in its entirety by reference.

Amongst the quaternary ammonium polymers, those which are particularly preferred include the homopolymer of dimethyldiallyl-ammonium chloride having a molecular weight of less than 100,000, such as that sold under the tradename MERQUAT 100 by Merck, and the copolymer of dimethyldiallylammonium chloride and acrylamide, having a molecular weight of more than 500,000, such as that sold under the tradename MERQUAT 550.

In the compositions according to the present invention, the polyamino-amides are generally present in an amount from 0.1 to 5%, preferably 0.1 to 3%, by weight, and the quaternized polymers are generally present in an amount from 0.1 to 10%, preferably 0.1 to 5%, by weight, based on the total weight of the composition.

In addition to the polyamino-amides and the quaternised polymers defined above, the compositions according to the present invention can contain adjuvants which are conventionally employed in cosmetic compositions for the hair, for example perfumes, colorants, preservatives, sequestering agents, thickeners and emulsifiers.

The compositions of this invention are more particularly in the form of treatment creams which can be applied before or after dyeing or coloring or bleaching, before or after shampooing or before or after permanent waving. They can however also be in the form of dyes or colouring products, shampoos, rinse lotions to be applied before or after shampooing, before or after colouring or bleaching or before or after permanent waving, or in the form of wave-setting lotions, brushing lotions and restructuring lotions.

When the compositions according to the present invention constitute such treatment creams they are generally based on soaps or on fatty alcohols, in the presence of emulsifiers.

Typically the soaps are formed from natural or synthetic fatty acids having from 12 to 18 carbon atoms, such as lauric acid, myristic acid, palmitic acid, oleic acid, ricinoleic acid, stearic acid and isostearic acid, and from alkalizing agents such as sodium hydroxide, potassium hydroxide, ammonia, monoethanolamine, diethanolamine and triethanolamine. They are preferably present in an amount from 10 to 30% by weight.

In addition to the mixture of quaternary polymers, polyamino-amides and soap, these creams can contain adjuvants which are usually employed in such compositions, such as fatty amides and fatty alcohols. Suitable fatty amides include the mono- or diethanolamides of acids derived from copra, of lauric acid or of oleic acid, in particular oleyl diethanolamide, copra mono- or diethanolamide and stearyl monoethanolamide, and they are preferably present in an amount up to 10% by weight.

Suitable fatty alcohols include oleyl, myristyl, cetyl, stearyl and isostearyl alcohol, and they are preferably present in an amount up to 10% by weight.

The creams can also be formulated from natural or synthetic alcohols having, for example, 12 to 18 carbon atoms, mixed with emulsifiers. Typical fatty alcohols include those derived from copra fatty acids, myristyl alcohol, cetyl alcohol, stearyl alcohol and hydroxystearyl alcohol, the alcohols generally being present in an amount from 5 to 25% by weight.

Suitable emulsifiers which can be used for this purpose include oxyethyleneated or polyglycerolated fatty alcohols such as polyoxyethyleneated oleyl alcohol derived from 10 mols of ethylene oxide (per mole of alcohol), stearyl alcohol containing 10, 15 or 20 mols of ethylene oxide, polyglycerolated oleyl alcohol containing 4 mols of glycerol, and synthetic fatty alcohols containing 9 to 15 carbon atoms, which are polyoxyethyleneated with 5 or 10 mols of ethylene oxide. These non-ionic emulsifiers are suitably present in an amount from 5 to 25% by weight.

Other emulsifiers which can be used include alkylsulphates, which may or may not be oxyethyleneated, such as sodium lauryl-sulphate, ammonium lauryl-sulphate, sodium cetyl-/stearyl-sulphate, triethanolamine cetyl-/stearylsulphate, monoethanolamine lauryl-sulphate, oxyethyleneated sodium lauryl-ether-sulphate containing for example, 2.2 molar units derived from ethylene oxide, and oxyethyleneated monoethanolamine lauryl-ether-sulphate containing, for example, 2.2 mols of ethylene oxide. These constituents are preferably present in an amount from 3 to 15% by weight.

The pH of the creams is generally from 3 to 9, and preferably from 5 to 9. When the compositions are in the form of coloring creams, they contain, in addition to the ingredients mentioned an alkalizing agent such as ammonia, monoethanolamine, diethanolamine or triethanolamine and a colorant. The pH of these compositions is generally from 9 to 11.

Suitable colorants include oxidation dyestuffs, to which direct dyestuffs, such as azo dyestuffs, anthraquinone dyestuffs, nitrobenzene dyes, indamines, indoanilines, indophenols and/or other oxidation dyestuffs such as leuco-derivatives of these compounds, can be added.

The oxidation dyestuffs are generally aromatic compounds of the diamine, aminophenol or phenol type.

They are not generally dyestuffs in themselves, but are converted into dyestuffs by condensation in the presence of an oxidizing medium, generally hydrogen peroxide. These oxidation dyestuffs are separated into, on the one hand, bases which are so-called "para or ortho derivatives" being diamines or mono- or di-aminophenols, and, on the other hand, compounds called "modifiers" or "couplers", which are so-called "meta derivatives", being meta-diamines, m-aminophenols or polyphenols.

The preferred oxidation bases are p-phenylenediamines which are optionally substituted on the nitrogen atom or on the aromatic nucleus by groups such as alkyl groups preferably having 1 to 4 carbon atoms, hydroxyalkyl groups preferably having 1 to 4 carbon atoms, halogen groups, and alkoxy groups preferably having 2 to 4 carbon atoms. Amongst these compounds, p-phenylenediamine, p-toluylenediamine, chloro-p-phenylenediamine and p-aminodiphenylamine may be particularly mentioned. It is also possible to use ortho derivatives such as o-phenylenediamine, o-toluylenediamine, 2,5-diaminoanisole, o-aminophenol and p-aminophenol.

The couplers which are particularly used are m-phenylenediamine, m-toluylenediamine, 2,4-diaminoanisole, m-aminophenol, pyrocatechol, resorcinol, hydroquinone, α-naphthol, 1,5-dihydroxynaphthalene and 2,6-diaminopyridine.

When the compositions according to the present invention are in the form of shampoos, they contain, in addition to the quaternized polymer and the crosslinked polyamino-amide, at least one anionic, cationic, non-ionic or amphoteric detergent.

Suitable anionic surface-active agents include the alkali metal salts, magnesium salts, ammonium salts, amine salts or aminoalcohol salts of the following anions and compounds:

alkyl-sulphates, alkyl-ether sulphates, the alkyl radical of which is a linear chain containing 12 to 18 carbon atoms, oxyethyleneated alkylamide-sulphates and -ether-sulphates containing linear chains having 12 to 18 carbon atoms, alkylaryl-polyether-sulphates and monoglyceride-sulphates, alkylsulphonates, the alkyl radical of which is a linear chain containing 12 to 18 carbon atoms, alkylamidesulphonates, alkylarylsulphonates, and α-olefine-sulphonates containing linear chains having 12 to 18 carbon atoms, alkyl-sulphosuccinates, alkyl-ether-sulphosuccinates, and alkylamide-sulphosuccinates, the alkyl radical of which consists of a linear chain preferably having 12 to 18 carbon atoms, alkyl-sulphosuccinamates, the alkyl radical of which has a linear chain containing 12 to 18 carbon atoms, alkyl-sulphoacetates, the alkyl radical of which contains a linear chain having 12 to 18 carbon atoms, alkyl-phosphates, and alkyl-ether-phosphates, the alkyl radical of which has a chain of 12 to 18 carbon atoms, alkylsarcosinates, alkylpolypeptidates, alkylamidopolypeptidates, alkylisethionates, and alkyl laurates, the alkyl radical of which has a chain of 12 to 18 carbon atoms, and fatty acids such as oleic acid, ricinoleic acid, palmitic acid, stearic acid, acids of copra oil or of hydrogenated copra oil, and carboxylic acids of polyglycol ethers corresponding to the formula:

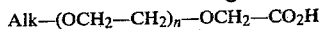
$$Alk-(OCH_2-CH_2)_n-OCH_2-CO_2H$$

in which the Alk substituent corresponds to a linear chain having from 12 to 18 carbon atoms, and n is an integer from 5 to 15, as well as mixtures of these.

Amongst the cationic surface-active agents which can be used singly or as mixtures, there may be mentioned, in particular, fatty amine salts such as alkylamine acetates, quaternary ammonium salts such as the chlorides or bromides of alkyldimethylbenzylammonium, alkyltrimethylammonium, alkyldimethylammonium, alkyldimethylhydroxyethylammonium and dimethyldistearylammonium, and alkylamidoethyltrimethylammonium methosulphates, alkylpyridinium salts and imidazoline derivatives. The alkyl radicals in these compounds preferably have from 1 to 22 carbon atoms. Compounds having a cationic character, such as amine oxides like alkyldimethylamine oxides or alkylaminoethyl-dimethylamine oxides, may also be mentioned.

Amongst the non-ionic surface-active agents which can be used in mixtures with the abovementioned anionic surface-active agents, there may be mentioned the products resulting from the condensation of a monoalcohol, an α-diol, an alkylphenol or an amide with glycidol, such as the products corresponding to the formula:

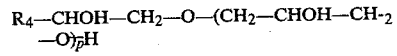
$$R_4-CHOH-CH_2-O-(CH_2-CHOH-CH_2-O)_pH$$

in which $R_4$ denotes an aliphatic, cycloaliphatic or arylaliphatic radical, preferably having 7 to 21 carbon atoms, and their mixtures, it being possible for the aliphatic chains to contain ether, thioether or hydroxymethylene links, and p has a statistical average value from 1 to 10 inclusive, and products corresponding to the formula:

$$R_5O[C_2H_3O(CH_2OH)]_q-H$$

in which $R_5$ denotes an alkyl, alkenyl or alkylaryl radical, and q has a statistical value of from 1 to 10 inclusive. Other such compounds are alcohols, alkylphenols, and polyoxyethyleneated or polyglycerolated fatty acids having a linear fatty chain containing 8 to 18 carbon atoms and most frequently containing units derived from 2 to 15 mols of ethylene oxide per mole of alcohol, phenol or acid. Ethylene oxide/propylene oxide copolymers, condensates of ethylene oxide and propylene oxide with fatty alcohols, polyoxyethyleneated fatty amides, polyoxyethyleneated fatty amines, ethanolamides, glycol fatty acid esters, sorbitol fatty acid esters and sucrose fatty acid esters may also be mentioned.

Preferred compositions of this type are those containing at least one quaternized polymer and one polyaminoamide, preferably the compounds sold under the tradenames MERQUAT 100 and 550 and CARTARETINE F, $F_4$ or $F_8$, with a non-ionic surface-active agent of the formula:

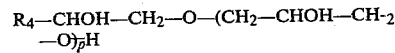
$$R_4-CHOH-CH_2-O-(CH_2-CHOH-CH_2-O)_pH$$

in which $R_4$ denotes a mixture of alkyl radicals having 9 to 12 carbon atoms, and p has a statistical value of about 3.5.

Suitable amphoteric surface-active agents include alkylamino-mono- and di-propionates, betains such as N-alkylbetains, N-alkylsulphobetaines and N-alkylamidobetaines, and cycloimidinium compounds such as alkylimidazolines. The alkyl group in these surface-active agents preferably has 1 to 22 carbon atoms.

All these well-known detergents, as well as all the other detergents which can be used in shampoos, can be employed in the compositions according to the present invention.

The shampoos can also contain various adjuvants such as perfumes, colorants, preservatives, thickeners, foam stabilizers, softening agents and also one or more cosmetic resins.

In these shampoos, the concentration of detergent is generally from 3 to 50%, preferably from 3 to 20%, by weight relative to the total weight of the composition; the pH is generally from 3 to 9, preferably from 7 to 9.

The compositions according to the invention can also be in the form of lotions which can be styling lotions or shaping lotions which may also be called brushing lotions, non-rinsed reinforcing wave-setting lotions and rinsed lotions which are also called rinses.

The terms "shaping lotions" or "brushing lotions" are to be understood as meaning lotions which are applied after shampooing and which assist the shaping of the head of hair, this shaping process being carried out on the wet hair using a brush, at the same time as the hair is dried using a handheld dryer.

The term "non-rinsed reinforcing wave-setting lotions" is to be understood as meaning a lotion which is applied after shampooing and before wave-setting; this lotion, which is not removed by rinsing, facilitates the subsequent wave-setting process and prolongs the life of the set.

These lotions may comprise, generally in aqueous, alcoholic or aqueous-alcoholic solution, apart from the essential quaternized polymer and crosslinked polyamino-amide, film-forming polymers such as polyvinylpyrrolidone, vinylpyrrolidone/vinyl acetate copolymers and vinyl acetate/vinyl alkyl ether copolymers.

Preferred resins include polyvinylpyrrolidone having a molecular weight of 10,000 to 70,000, vinylpyrrolidone(PVP)/vinyl acetate(VA) copolymers having a molecular weight of 30,000 to 200,000, the ratio of PVP:VA being from 30:70 to 70:30, terpolymers of methyl methacrylate (15–25%), stearyl methacrylate (18–26%) and dimethylaminoethyl methacrylate, optionally quaternized by dimethyl sulphate (52–62%), quaternary vinylpyrrolidone copolymers such as the polymer having a molecular weight of the order of 1,000,000, sold under the trademark "GAFQUAT 755" by GAF CORPORATION, and the polymer having a molecular weight of the order of 100,000, sold under the trademark "GAFQUAT 734", cationic graft copolymers resulting from the copolymerization of 3 to 95% by weight of N-vinylpyrrolidone, 3 to 95% by weight of diethylaminoethyl methacrylate which may or may not be quaternized, and 2 to 50% by weight of polyethylene glycol, such as those described U.S. patent application Ser. No. 690,783, now U.S. Pat. No. 4,047,888, cationic polymers, which may or may not be quaternized, resulting from the condensation of piperazine or its derivatives (1) with bifunctional compounds such as alkyl or alkylaryl dihalides, bis-epoxides, epihalogenohydrins, bis-unsaturated derivatives, and their oligomers, and/or (2) with a primary amine, the two hydrogen atoms of which can be substituted and which behaves as a bifunctional compound, or (3) both with an epihalogenohydrin and with a hydroxylic amine such as diglycolamine or 2-amino-2-methylpropane-1,3-diol, or with an amino-acid such as glycocoll, and quaternized celluloses such as "JR 400" sold by Messrs. UNION CARBIDE.

In these solutions, the concentration of polymer is generally from 0.1 to 5%, preferably from 0.1 to 3%, by weight and the pH is generally from 3 to 9.

The rinsed lotions may be applied before or after coloring (dyeing), before or after bleaching, before or after permanent waving, before or after shampooing or between the two stages of shampooing, in order to obtain a hair conditioning effect; they can be rinsed out after remaining on the hair for the desired period of time.

These compositions are suitably aqueous or aqueous-alcoholic solutions optionally comprising surface-active agents, or they can be emulsions or gels. They can also be pressurized in the form of an aerosol.

The surface-active agents which can be used are essentially non-ionic or cationic surface-active agents of the type described above for the shampoo compositions and, in particular, products resulting from the condensation of a monoalcohol, an α-diol, an alkylphenol or an amide with glycidol, such as products of the formula:

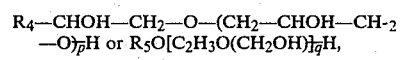

$R_4$—CHOH—CH$_2$—O—(CH$_2$—CHOH—CH$_2$—O$)_{\overline{p}}$H or $R_5$O[C$_2$H$_3$O(CH$_2$OH)$]_{\overline{q}}$H, as defined above. Particularly preferred for use is the non-ionic surface-active agent of the formula:

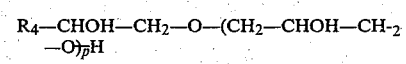

$R_4$—CHOH—CH$_2$—O—(CH$_2$—CHOH—CH$_2$—O$)_{\overline{p}}$H in which $R_4$ denotes a mixture of alkyl radicals having 9 to 12 carbon atoms, and p has a statistical value of about 3.5, which is suitably present in the composition in an amount of 0.5 to 7% by weight.

It is also possible to use alcohols, alkylphenols, and polyoxyethyleneated or polyglycerolated fatty acids containing a linear fatty chain having 8 to 18 carbon atoms and most frequently containing units derived from 2 to 15 mols of ethylene oxide. The concentration of surface-active agents is generally from 0 to 7% by weight.

Anionic or amphoteric surface-active agents can be added to these compositions.

When these compositions are in the form of an emulsion, they can be non-ionic or anionic. The non-ionic emulsions principally comprise a mixture of oils and/or waxes, fatty alcohols, and polyoxyethyleneated fatty alcohols such as polyoxyethyleneated stearyl or cetyl/stearyl alcohol. Cations such as, for example, those defined above can be added to these compositions.

The anionic emulsions are generally formed from soaps. Thus, there may be mentioned the emulsion comprising selfemulsifying glycerol stearate sold under the tradename IMWITOR 960 K by Messrs. DYNAMIT NOBEL, and the emulsions comprising a combination of glycerol monostearate with citric acid esters, with fatty alcohols and lipopeptides or with alkali metal stearates, sold respectively under the tradenames LAMEFORM ZEM, PLM and NSM by Messrs. GRUNAU.

When the compositions are in the form of gels, they contain thickeners and, if desired, solvents. Suitable thickeners include sodium alginate, gum arabic and cellulose derivatives such as methylcellulose, hydroxymethylcellulose, hydroxyethylcellulose and hydroxypropylcellulose. It is also possible to obtain a thickener for the lotions by mixing polyethylene glycol with polyethylene glycol stearate or distearate, or by mixing phosphoric esters with amides.

The concentration of thickeners is generally from 0.5 to 30%, preferably from 0.5 to 15%, by weight. The pH of the rinsed lotions or "rinses" is generally from 2 to 9.5

When such compositions are pressurized in the form of an aerosol, propellant gases which may be used include carbon dioxide, nitrogen, nitrous oxide, volatile hydrocarbons such as butane, isobutane and propane, or, preferably, fluorinated hydrocarbons, in particular fluorochlorohydrocarbons such as dichlorodifluoromethane or "Freon" 12, dichlorotetrafluoroethane or "Freon" 114 and trichloromonofluoromethane or "Freon" 11. These propellants can be used by themselves or in combination, and, in particular, a mixture of Freon 114/12, in proportions varying from 40:60 to 80:20, can be employed.

Finally, the compositions according to the present invention can constitute restructing lotions and contain products which strengthen the keratin chain of the hair. For this purpose, methylol-type derivatives, and especially products of the type described in U.S. Pat. No. 3,773,056 the disclosure of which is hereby incorporated in their entirety by reference, can be used.

The perfumes which can be used in these compositions are cosmetically acceptable perfumes and they are generally present in amounts from 0.1 to 0.5% by weight.

The colorants intended to impart a coloration to the compositions according to the invention are generally present in an amount from 0.001 to 0.5% by weight.

The following Examples further illustrate the present invention. In these Examples, the amount of Cartarétine and Merquat used are always in active material. Merquat 100 is in the form of a 40% solution, Merquat 550 is in the form of an 8% solution and the various Cartarétines are in the form of 30% solutions. The general term "colorant" relates to colorants which serve the purpose of coloring the compositions with a view to improving their appearance, and they therefore have no effect on the properties of the compositions themselves when the latter are applied to the hair.

EXAMPLE 1

An emulsion having the following composition is prepared:

| | |
|---|---|
| Vaseline oil: | 15 g |
| Lanette wax: | 2.5 g |
| Polyoxyethyleneated cetyl/stearyl alcohol containing 10 mols of ethylene oxide, sold under the tradename: SIMULSOL 1951 D (MONTANOIR): | 2.5 g |
| Cartarétine F$_4$: | 0.5 g |
| Merquat 100: | 0.3 g |
| Water q.s.p.: | 100 g |

The emulsion thus obtained has a pH of 8.3 and a viscosity of 25-30 cP. This emulsion can be used for rinse treatments which are also called "rinses".

This emulsion is applied to the hair and, after remaining on the hair for a few minutes, it is rinsed out.

The hair is easy to comb out, supple and light. It is very springy.

EXAMPLE 2

A rinse treatment having the following composition is prepared:

| | |
|---|---|
| Polyoxyethylenated lauryl alcohol containing 15 mols of ethylene oxide: | 0.7 g |
| Cartarétine F$_4$: | 0.9 g |
| Merquat 100: | 0.3 g |
| Water q.s.p.: | 100 g |

The pH is adjusted to 6 with lactic acid.

This treatment is applied by allowing it to remain on the hair for a few minutes before shampooing in the conventional manner.

The hair is much easier to comb out and very springy.

EXAMPLE 3

The following composition is prepared:

| | |
|---|---|
| R$_4$—CHOH—CH$_2$—O—(CH$_2$—CHOH—CH$_2$—O)$_p$H; R$_4$ is a mixture of alkyl chains having 9 to 12 carbon atoms and p is equal to 3.5: | 0.7 g |
| Merquat 100: | 0.5 g |
| Cartarétine F$_4$: | 0.7 g |
| Acid phosphoric ester of oxyethylenated oleyl alcohol sold under the tradename Divalin SO by Messrs. ZSCHIMMER & SCHWARZ: | 0.4 g |
| Water q.s.p.: | 100 cc |

The pH is adjusted to 7.5 with lactic acid.

This composition is used as a rinse lotion or "rinse".

It is applied to hair which has been washed beforehand, and it is found that the hair thus treated is very easy to comb out.

When dry, the hair is particularly bulky, glossy and easy to style.

EXAMPLE 4

A rinse treatment having the following composition is prepared:

| | |
|---|---|
| R$_4$—CHOH—CH$_2$—O—CH$_2$—CHOH—CH$_2$—O)$_p$H; R$_4$ is a mixture of alkyl chains having from 9 to 12 carbon atoms, and p is equal to 3.5: | 0.5 g |
| Merquat 550: | 0.3 g |
| Cartarétine F$_8$: | 0.7 g |
| Perfume: | 0.1 g |
| Colorant: | 0.01 g |
| Water q.s.p.: | 100 g |

The pH is adjusted to 8.6 with lactic acid.

This product is applied to the hair before shampooing.

It is allowed to remain on the hair for a few minutes and is then rinsed out.

The hair is easier to comb out and has a pleasant feel which is both hard and soft; the style has improved springiness.

EXAMPLE 5

The following composition is prepared:

| | |
|---|---|
| Cartarétine F$_4$: | 0.3 g |
| Merquat 100: | 0.3 g |
| Quaternary vinylpyrrolidone copolymer having a molecular weight of 1,000,000, marketed under the name Gafquat 734 by Messrs. General Aniline: | 0.5 g of active material |
| Ethyl alcohol q.s.p.: | 10° |
| Perfume: | 0.3 g |
| Colorant: | 0.015 g |
| Water q.s.p.: | 100 cc |

The pH is adjusted to 6 with lactic acid.

This composition can be used as a wavesetting lotion. When applied to hair which has been washed, this lotion makes the hair easier to comb out.

After drying and wavesetting, the hair is glossy, soft and easy to style.

EXAMPLE 6

The following composition is prepared:
| | |
|---|---|
| Cartarétine F$_4$: | 0.2 g |
| Merquat 100: | 0.7 g |
| Trimethylcetylammonium bromide: 0.2 g of active material | |
| Perfume: | 0.1 g |
| Colorant: | 0.15 g |
| Water q.s.p.: | 100 cc |

The pH is adjusted to 7 with lactic acid.

This composition is used as a wavesetting lotion.

When applied to natural hair, this lotion makes the wet hair easier to comb out.

When dry, the hair is glossy and easy to style.

This lotion can also be used as a brushing lotion.

EXAMPLE 7

The following composition is prepared:
| | |
|---|---|
| Cartarétine F$_4$: | 0.2 g |
| Merquat 550: | 0.04 g |
| Trimethylcetylammonium bromide: 0.2 g of active material | |
| Perfume: | 0.15 g |
| Colorant: | 0.1 g |
| Water q.s.p.: | 100 cc |

The pH is adjusted to 6 with lactic acid.

This composition is used as a brushing lotion.

When applied to hair which has been colored, this lotion makes the wet hair easier to comb out.

When styling the hair according to the brushing technique, it is found that this lotion enables the brush to pass more easily through the hair and leaves the hair soft and glossy and with a good hold.

EXAMPLE 8

A non-ionic shampoo having the following composition is prepared:
| | |
|---|---|
| R$_4$—CHOH—CH$_2$—O—(CH$_2$—CHOH—CH$_2$—O—)$_p$H; R$_4$ is a mixutre of alkyl chains having from 9 to 12 carbon atoms, and p is equal to 3.5 | 10 g |
| Copra diethanolamide: | 2 g |
| Cartarétine F$_4$: | 0.6 g |
| Merquat 100: | 0.3 g |
| Perfume: | 0.1 g |
| Colorant: | 0.05 g |
| Water q.s.p.: | 100 g |

The pH is 7 (without adjustment).

This shampoo is in the form of a clear liquid.

When applying this shampoo to natural hair according to the usual technique, it is found that the wet hair is easy to comb out and that the hair is soft. When dry, the hair is glossy and manageable.

EXAMPLE 9

An anionic shampoo having the following composition is prepared:
| | |
|---|---|
| C$_{12}$–C$_{14}$ alcohol which is oxyethyleneated with 10 mols of ethylene oxide and is carboxymethylated, sold under the tradename AKYPO RLM 100 by Messrs. CHEM Y: | 3 g |
| Polyxoyethyleneated lauryl alcohol containing 12 mols of ethylene oxide: | 7 g |
| Lauryl diethanolamide: | 3 g |
| Cartarétine F$_4$: | 0.5 g |
| Merquat 100: | 0.3 g |
| Perfume: | 0.15 g |
| Colorant: | 0.07 g |
| Water q.s.p.: | 100 g |

The pH is 7.2 (without adjustment).

This shampoo is in the form of a clear liquid. It is applied to dyed hair and it is found that the wet hair is easier to comb out and that the shampoo makes the hair soft. When dry, the hair is springy and bulky.

EXAMPLE 10

A cationic shampoo having the following composition is prepared:
| | |
|---|---|
| Alkyl(C$_{12}$–C$_{18}$)dimethylcarboxymethylammonium hydroxide sold by Messrs. HENKEL under the tradename: DEHYTON AB 30: | 10 g |
| Polyoxyethyleneated lauryl alcohol containing 12 mols of ethylene oxide: | 5 g |
| Lauryl diethanolamide: | 2 g |
| Cartarétine F$_4$: | 0.7 g |
| Merquat 100: | 0.5 g |
| Perfume: | 0.1 g |
| Colorant: | 0.1 g |
| Water q.s.p.: | 100 g |

The pH is 5 (without adjustment).

This shampoo is in the form of a clear liquid. It is applied to dyed hair.

The wet hair is light.

When dry, the hair is springy and bulky.

EXAMPLE 11

An anionic shampoo having the following composition is prepared:
| | |
|---|---|
| C$_{12}$–C$_{14}$ alcohol which is oxyethyleneated with 10 moles of ethylene oxide and is carboxymethylated, sold under the tradename AKYPO RLM 100 by Messrs. CHEM Y: | 3 g |
| Polyoxyethyleneated lauryl alcohol containing 12 mols of ethylene oxide: | 7 g |
| Lauryl diethanolamide: | 3 g |
| Cartarétine F: | 0.4 g |
| Merquat 550: | 0.1 g |
| Perfume: | 0.1 g |
| Colorant: | 0.15 g |
| Water q.s.p.: | 100 g |

The pH of this anionic shampoo is equal to 7.

This shampoo is in the form of a clear liquid. It is applied to natural hair.

The wet hair is easy to comb out and the hair is soft. When dry, the hair is springy and bulky.

EXAMPLE 12

A cationic shampoo having the following composition is prepared:
| | |
|---|---|
| Alkyl(C$_{12}$–C$_{18}$)dimethylcarboxymethylammonium hydroxide sold by Messrs. HENKEL under the tradename DEHYTON AB 30: | 10 g |
| Polyoxyethyleneated lauryl alcohol containing 12 mols of ethylene oxide: | 5 g |
| Lauryl diethanolamide: | 2 g |
| Cartarétine F$_8$: | 0.7 g |
| Merquat 550: | 0.5 g |
| Perfume: | 0.2 g |
| Colorant: | 0.015 g |
| Water q.s.p.: | 100 g |

The pH of this composition is equal to 5.

This shampoo is in the form of a clear liquid. It is applied to permed dyed hair.

The wet hair is light.

When dry, the hair is springy and bulky.

EXAMPLE 13

The following composition is prepared:

| | |
|---|---|
| Cetyl alcohol: | 22 g |
| Oxyethyleneated cetyl alcohol containing 10 moles of ethylene oxide, sold under the name BRIJ 56 by Messrs. ATLAS: | 12 g |
| Merquat 100: | 5 g |
| Cartarétine F: | 3 g |
| Acid phosphoric ester of oxyethyleneated oleyl alcohol, sold under the tradename Divaline SO NEU by Messrs. ZSCHIMMER & SCHWARZ: | 2 g |
| Water q.s.p.: | 100 g |

This composition is in the form of a cream which can be applied for deep care.

This cream is applied to clean hair, which is damp and has been dried without heat, in a sufficient amount (60 to 80 g) to thoroughly impregnate and cover the head of hair.

It is allowed to remain on the hair for 30 to 40 minutes and is rinsed out.

The wet hair is very soft and easy to comb out.

The hair is set in waves and dried under a dryer. When dry, the hair is easy to comb out and has a silky feel; it is glossy, springy and has body and volume.

EXAMPLE 14

| | |
|---|---|
| Stearyl alcohol: | 15 g |
| Copra monoethanolamide: | 4 g |
| Sodium cetyl-/stearyl-sulphate: | 2 g |
| Merquat 550: | 30 g |
| Cartarétine F$_4$: | 2.5 g |
| Water q.s.p.: | 100 g |

This composition can be used as a treatment cream after coloring by oxidation.

10-15 g of this cream are applied to damp hair after the product for coloring by oxidation has been rinsed out.

It is allowed to remain on the hair for 2 to 3 minutes and is rinsed out. The wet hair is easy to comb out and has a soft feel.

The hair is set in waves and dried under a dryer. When dry, the hair is easy to comb out and has a silky feel; it is glossy, springy and has volume and body.

EXAMPLE 15

The following composition is prepared:

| | |
|---|---|
| Cetyl/stearyl alcohol: | 15 g |
| Stearic acid: | 3 g |
| 22° C. Baume strength ammonia solution: | 12 ml |
| Oxyethyleneated stearyl alcohol containing 10 mols of ethylene oxide, sold under the name BRIJ 76 (ATLAS): | 4 g |
| Merquat 100: | 7 g |
| Cartarétine F$_8$: | 6 g |

This composition is used as a dyeing carrier.

The following coloring composition is added thereto:

| | |
|---|---|
| m-Diaminoanisole sulphite: | 0.048 g |
| Resorcinol: | 0.420 g |
| m-Aminophenol base: | 0.150 g |
| Nitro-p-phenylenediamine: | 0.085 g |
| p-Toluylenediamine: | 0.004 g |
| Trilone B (ethylenediaminetetraacetic acid): | 1.000 g |
| Sodium bisulphite solution d=1.3: | 1.200 g |
| Water q.s.p.: | 100 g |

30 g of this formula are mixed in a bowl with 45 g of hydrogen peroxide of 20 volumes strength. A smooth, consistent cream is obtained which is pleasant to apply and which adheres well to the hair.

This cream is applied to the hair using a paint-brush.

It is allowed to remain on the hair for 30 minutes and rinsed out.

The hair is easy to comb out and the feel is silky.

The hair is set in waves and dried.

The hair is glossy and springy; it has body and volume; the feel is silky and the hair is easy to comb out.

On hair which is 100% white, a blond coloration is obtained.

We claim:

1. A cosmetic composition suitable for treating the hair which comprises: (a) from about 0.1 to about 5.0 percent by weight, based on the weight of the entire composition, of at least one water-soluble polyaminoamide derivative which is a condensation product of a polyalkylenepolyamine with a polycarboxylic acid, which has been alkylated with a bifunctional alkylating agent having the formula:

$$A-CH_2-\overset{+}{\underset{\underset{\displaystyle }{|}}{N}}\overset{R_1}{\underset{R_2}{\diagup}} \left[ B-\overset{+}{\underset{\underset{\displaystyle }{|}}{N}}\overset{R_1}{\underset{R_2}{\diagup}} \right]_x CH_2-A$$

in which x is 0 or an integer from 1 to 7, A denotes a $$-CH\underset{O}{\overset{\diagdown\diagup}{-}}CH_2 \quad or \quad \overset{\diagdown}{C}H-CH_2 \atop \underset{OH\quad R_3}{| \quad\quad |}$$

group in which R$_3$ denotes halogen, R$_1$ and R$_2$ denote independently of one another, an alkyl or hydroxyalkyl group containing 1 to 4 carbon atoms, and B represents an alkylene group containing 2 to 6 carbon atoms, a $$-CH_2-\underset{\underset{\displaystyle OH}{|}}{CH}-CH_2-$$

group or a group of formula —(CH$_2$)$_y$—NH—CO—NH—(CH$_2$)$_y$— in which y is an integer from 1 to 4; (B) from about 0.1 to about 10.0 percent by weight, based on the weight of the entire composition of at least one water-soluble high molecular weight quaternary ammonium polymer containing chain units of the formula:

$$\left[ -CH_2-R''C\underset{H_2C}{\overset{CH_2}{\diagup}}\underset{\underset{\displaystyle R\quad R'}{\overset{+}{N}}}{\overset{\diagdown}{\diagup}}\overset{CR''-}{\underset{CH_2}{\diagdown}} \right]_n$$

in which R'' denotes a hydrogen atom or a methyl group, and R and R' denote, independently of one another, an alkyl group having from 1 to 22 carbon atoms, a hydroxyalkyl group, or a lower amidoalkyl group, or R and R', together with the nitrogen atom to which they are bonded, denote an heterocyclic group, said units being associated with a cosmetically acceptable anion; and (C) a sufficient amount of a carrier to constitute 100 percent by weight for the total composition in order to form an aqueous solution, an aqueous alcoholic solution, an aqueous-alcoholic-surface active agent solution, an emulsion, a cream, a gel or an aerosol.

2. A composition according to claim 1, in which the polyalkylene-polyamine is a dialkylenetriamine.

3. A composition according to claim 1, in which the polycarboxylic acid is a dicarboxylic acid of the formula:

$$HOOC-C_mH_{2m}-COOH$$

in which m denotes an integer from 4 to 8.

4. A composition according to claim 36 in which the dicarboxylic acid is adipic acid.

5. A composition according to claim 1, in which the molar ratio of the polyalkylene-polyamine to the carboxylic acid is from 4:5 to 6:5.

6. A composition according to claim 1 in which A is $$-CH\underset{O}{\overset{}{\diagdown\diagup}}CH_2,$$

$R_1$ and $R_2$ are alkyl, and x is equal to 0.

7. A composition according to claim 6 in which $R_1$ and $R_2$ are methyl.

8. A composition according to claim 1, in which the polyamino-polyamide is an adipic acid/dimethylaminohydroxypropyldiethylenetriamine copolymer.

9. A composition according to claim 1, in which the polyamino-amide is present in an amount from about 0.1 to about 3.0 percent by weight based on the total weight of the composition.

10. A composition according to claim 1, in which the quaternary polymer is present in an amount from about 0.1 to about 5.0 percent by weight based on the total weight of the composition.

11. A composition according to claim 1 also containing at least one adjuvant selected from the group consisting of a perfume, colorant, preservative, sequestering agent, thickener and emulsifier.

12. A composition according to claim 1, which also contains a soap in an amount from 10 to 30% by weight, an emulsifier selected from the group consisting of an oxyethyleneated and a polyglycerolated fatty alcohol in an amount from 5 to 25% by weight, an oxyethyleneated alkyl-sulphate in an amount from 3 to 15% by weight, a fatty amide in an amount from 0 to 10% by weight, and a fatty alcohol present in an amount from 0 to 10% by weight; and an alkalizing agent.

13. A composition according to claim 1, which also contains a natural or synthetic alcohol having 12 to 18 carbon atoms in an amount from 5 to 25% by weight, an emulsifier which is an oxyethyleneated or polyglycerolated fatty alcohol in an amount from 5 to 25% by weight, an oxyethyleneated alkyl-sulphate in an amount from 3 to 15% by weight, and a fatty amide in an amount from 0 to 10% by weight.

14. A composition according to claim 12, having a pH from 3 to 9.

15. A composition according to claim 13, having a pH from 3 to 9.

16. A composition according to claim 12, which also contains a colorant selected from the group consisting of an oxidation dyestuff and a nitrobenzene dyestuff, the composition having a pH from 9 to 11.

17. A composition according to claim 1, which also contains at least one anionic, cationic, nonionic or amphoteric detergent in an amount from 3 to 50% by weight, and at least one adjuvant selected from the group consisting of a perfume, colorant, preservative, thickener, foam stabilizer, softening agent and an additional cosmetic resin other than those of claim 1, the pH being from 3 to 9.

18. A composition according to claim 17 which contains from 3 to 20% by weight of detergent.

19. A composition according to claim 17, having a pH from 7 to 9.

20. A composition according to claim 1, which also contains at least one nonionic or cationic surface active agent which is selected from the group consisting of: a condensation product of a monoalcohol; an alpha-diol; an alkylphenol or an amide with glycidol; and an alcohol, alkylphenol and polyoxyethyleneated or polyglycerolated fatty acid containing a linear fatty chain having from 8 to 18 carbon atoms; and which is present in an amount up to 7% by weight, the pH being from 2 to 9.4.

21. A composition according to claim 1, which contains a nonionic surface active agent of the formula:

$$R_4-CHOH-CH_2-O-(CH_2-CHOH-CH_2-O)_{\overline{p}}H$$

in which $R_4$ denotes a mixture of alkyl radicals having 9 to 12 carbon atoms, and p is about 3.5.

22. A composition according to claim 20, which additionally contains an anionic or amphoteric surface active agent.

23. A composition according to claim 1, which additionally contains a film-forming polymer other than those of claim 34, in an amount from 0.1 to 5% by weight, said carrier being water, alcohol or water-alcohol having a pH from 3 to 9.

24. A composition according to claim 23, which contains 0.1 to 3% by weight of the additional film-forming polymer.

25. A composition according to claim 1, which also contains a mixture of oils and waxes, fatty alcohols and polyoxyethyleneated fatty alcohols, or soap, said composition being an emulsion.

26. A composition according to claim 1, which also contains 0.5 to 15% by weight of thickener, said composition being a gel.

27. A composition according to claim 1, which also contains a methylol-type hair restructuring agent.

28. A cosmetic composition suitable for treating the hair which comprises: (A) from about 0.1 to about 5.0 percent by weight, based on the weight of the entire composition, of at least one water-soluble polyaminoamide derivative which is a condensation product of a polyalkylene-polyamine with a polycarboxylic acid, which has been alkylated with a bifunctional alkylating agent having the formula:

$$A-CH_2-\underset{+}{N}\underset{R_2}{\overset{R_1}{\diagdown\diagup}}\left[-B-\underset{+}{N}\underset{R_2}{\overset{R_1}{\diagdown\diagup}}\right]_x CH_2-A$$

in which x is 0 or an integer from 1 to 7, A denotes a

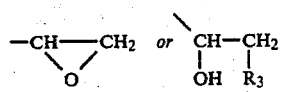

group in which $R_3$ denotes halogen, $R_1$ and $R_2$ denote independently of one another, an alkyl or hydroxyalkyl group containing 1 to 4 carbon atoms, and B represents an alkylene group containing 2 to 6 carbon atoms,

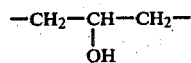

group or a group of formula $-(CH_2)_y-NH-CO-NH-(CH_2)_y-$ in which y is an integer from 1 to 4; (B) from about 0.1 to about 10.0 percent by weight, based on the weight of the entire composition of at least one water-soluble high molecular weight quaternary ammonium polymer which is a homopolymer of dimethyldiallylammonium chloride, having a molecular weight not exceeding 100,000; and (C) a sufficient amount of a carrier to constitute 100 percent by weight for the total composition in order to form an aqueous solution, an aqueous alcoholic solution, an aqueous-alcohol-surface active agent solution, an emulsion, a cream, a gel or an aerosol.

29. A cosmetic composition suitable for treating the hair which comprises: (A) from about 0.1 to about 5.0 percent by weight, based on the weight of the entire composition, of at least one water-soluble polyaminoamide derivative which is a condensation product of a polyalkylene-polyamine with a polycarboxylic acid, which has been alkylated with a bifunctional alkylating agent having the formula:

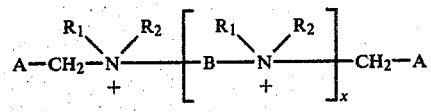

in which x is 0 or an integer from 1 to 7, A denotes a

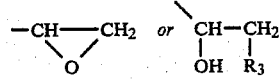

group in which $R_3$ denotes halogen, $R_1$ and $R_2$ denote independently of one another, an alkyl or hydroalkyl group containing 1 to 4 carbon atoms, and B represents an alkylene group containing 2 to 6 carbon atoms, a

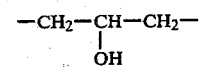

group or a group of formula $-(CH_2)_y-NH-CO-NH-(CH_2)_y-$ in which y is an integer from 1 to 4; (B) from about 0.1 to about 10.0 percent by weight, based on the weight of the entire composition of at least one water-soluble high molecular weight quaternary ammonium polymer which is a copolymer of dimethyldiallylammonium chloride and acrylamide, having a molecular weight not exceeding 500,000; and (C) a sufficient amount of a carrier to constitute 100 percent by weight for the total composition, in order to form an aqueous solution, an aqueous alcoholic solution, an aqueous-alcoholic-surface agent solution, an emulsion, a cream, a gel, or an aerosol.

30. A process for treating the hair, which comprises applying thereto a cosmetically effective amount of the composition of any one of claims 6–29 for conditioning the hair.

* * * * *